United States Patent [19]

Gelernt et al.

[11] 4,415,402

[45] Nov. 15, 1983

[54] END-POINT DETECTION IN PLASMA ETCHING OR PHOSPHOSILICATE GLASS

[75] Inventors: Barry Gelernt, Bridgeport; C. Wallace Wang, Wilton, both of Conn.

[73] Assignee: The Perkin-Elmer Corporation, Norwalk, Conn.

[21] Appl. No.: 250,375

[22] Filed: Apr. 2, 1981

[51] Int. Cl.³ .................... H01L 21/306; C03C 15/00
[52] U.S. Cl. .................................... 156/626; 156/643; 156/646; 156/656; 156/657; 156/659.1; 204/192 E; 356/72
[58] Field of Search ............... 156/626, 643, 646, 654, 156/655, 656, 657, 659.1, 662; 204/192 E, 298; 250/372, 373, 492.2; 356/316, 72

[56] References Cited

U.S. PATENT DOCUMENTS

| | | | |
|---|---|---|---|
| 3,880,684 | 4/1975 | Abe | 156/646 |
| 4,181,564 | 1/1980 | Fogarty et al. | 156/643 |
| 4,263,088 | 4/1981 | Gorin | 156/626 |
| 4,289,188 | 9/1981 | Mizutani et al. | 156/626 |
| 4,303,467 | 12/1981 | Scornavacca | 204/192 E |

*Primary Examiner*—William A. Powell
*Assistant Examiner*—Thomas Bokan
*Attorney, Agent, or Firm*—S. A. Giarratana; E. T. Grimes; T. P. Murphy

[57] ABSTRACT

A method for determining the completion of removal by plasma etching of phosphorus doped silicon dioxide from an underlying substrate.

3 Claims, 3 Drawing Figures

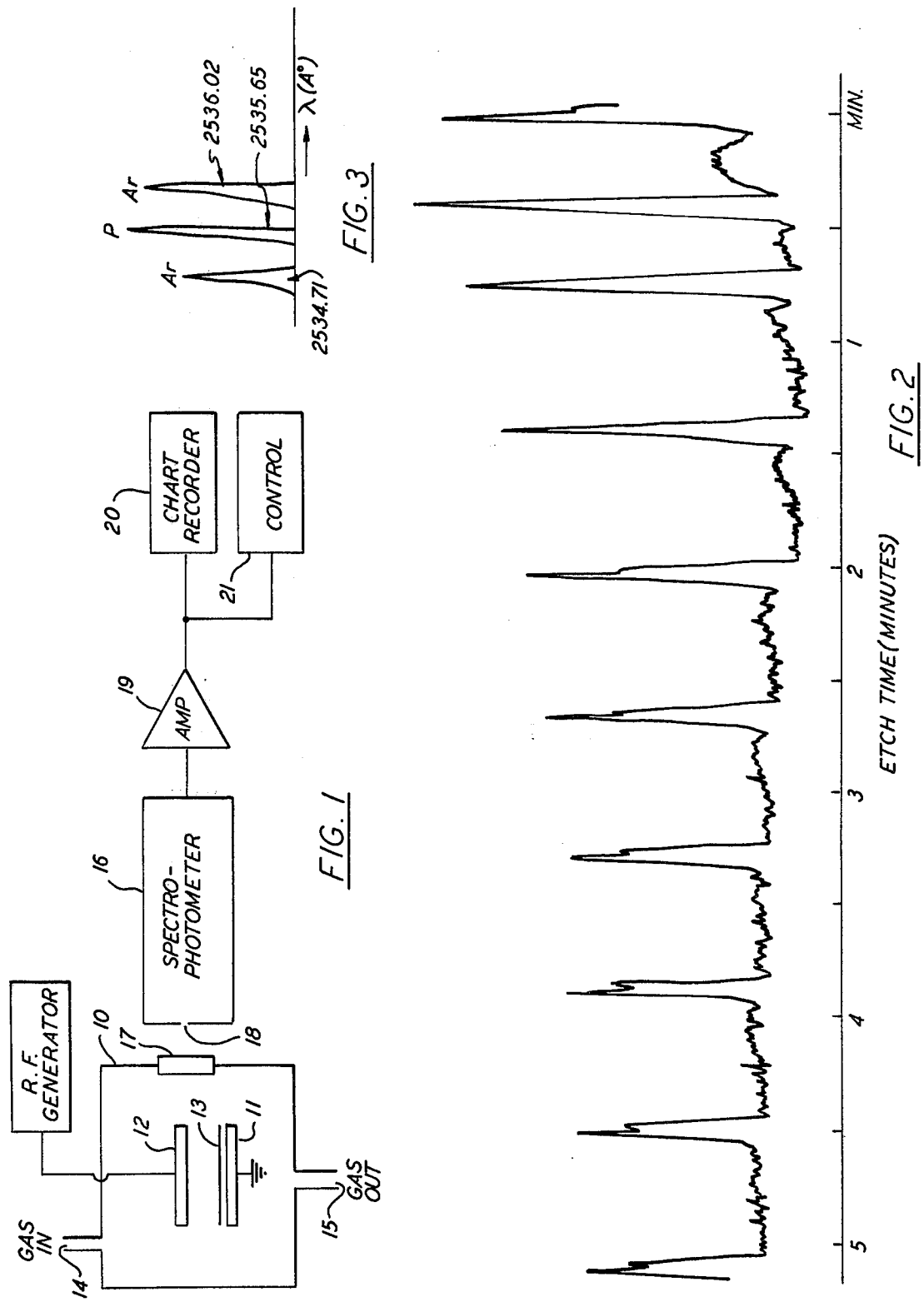

END-POINT DETECTION IN PLASMA ETCHING OR PHOSPHOSILICATE GLASS

BACKGROUND OF THE INVENTION

An important process in the fabrication of integrated circuits is the removal of various layers of materials formed on the silicon wafer. Such removal must be highly selective. First the removal of material is accomplished on a wafer containing a patterned coating of, for example, photoresist which permits removal of material only from selected areas of the wafer. At the same time the amount of material removed is critical. For example, only a particular layer of material should be removed without disturbing the underlying layer or substrate. Thus, it is important to know or detect when all of the selected material has been removed so that the process can be stopped before the substrate is damaged.

Several etching techniques are now in common usage. One such technique utilizes liquid chemicals into which a photoresist pattern silicon wafer is immersed in a chemical solution. The chemical attacks the material not covered by the photoresist. This method has the disadvantage of being isotropic, i.e., the edges on the etched surfaces are not well defined due to undercutting which is the etching away of the walls or that portion of the material covered on its surface by the photoresist.

With the demand for smaller geometries and line widths on integrated circuits a technique known as plasma or dry etching has been evolved. This method is anisotropic and eliminates undesirable undercutting. In this method a gas such as $CF_4$ is injected into a chamber containing the wafer to be etched. The chamber is maintained at a relative vacuum and the gas is turned into a plasma by coupling the chamber to an R.F. frequency power source. This creates radicals which are chemically reactive with the surface to be etched, thus, removing the desired material which is continuously removed from the chamber. Like all methods it is important to detect when the desired material is removed.

BRIEF SUMMARY OF THE INVENTION

The present method relates to a method for detecting the completion or end-point of an etching process. In particular, the present invention relates to the optical end-point detection of phosphorus doped silicon dioxide coated on a given substrate such as silicon wafer. In this method the wafer to be etched is placed in an etching chamber. At the start of the etching process the etching gas is spectroscopically observed to have a phosphorus atomic line accompanied by two Argon atomic lines. End-point occurs when the phosphorus atomic line is observed to disappear and the spectroscopic Argon "doublet" is observed to remain. Accurate detection of end-point permits automation of the etching process of phosphorous doped silicon dioxide.

BRIEF DESCRIPTION OF THE DRAWINGS

FIG. 1 is a block diagram of a system for carrying out the method of the present invention, FIG. 2 is a graphic representation of a time varying spectrum produced on the chart recorder of FIG. 1, FIG. 3 is a graphic representation of a portion of FIG. 2 at a higher resolution.

DESCRIPTION

FIG. 1 illustrates a system for carrying out the method of the present invention.

An etching chamber 10 has a pair of electrodes 11 and 12 disposed therein. Electrode 11 which is connected to ground has disposed thereon a wafer 13. For purposes of this invention the wafer 13 is coated with a thin layer, e.g., 1 $\mu$m of phosphorus doped silicon dioxide well known as P-Glass. P-Glass is an important material in integrated circuit fabrication and is used as a passivation layer on such devices. In actual fabrication of an integrated circuit the P-Glass may be circuit patterned on the wafer 13.

Electrode 12 is connected to a source of R.F. power. Etching gases from the FREON family (FREON is a registered trademark of the Dupont Co.), e.g., $CF_4$, $C_2F_6$ are injected into chamber 10 via port 14 and exit along with etching products via exit port 15. Gas flow control means (not shown) maintain the pressure in chamber 10 at approximately 1 Torr. The temperature is nominally 25° C. within chamber 10.

The R.F. power source which has a frequency in the megahertz range and a power in the 300 watts range causes the etching gas to become a plasma which attacks the P-Glass layer, removing it from the wafer in all unprotected areas.

The glow from the etching plasma is viewed by spectrometer 16 via a quartz glass view port 17 in the wall of chamber 10 and slit 18 of spectrometer 16. Spectrometer 16 may be a 0.5 Meter Ebert available from the Terral Ash Corporation. It is tunable over a wide spectrum and in the present case is turned to span the atomic line of phosphorus 2535.65Å. The output of spectrophotometer 16 is connected to chart recorder 20 and if desired to a control 21 via amplifier 19. The control 21 may be used to stop the etching process when all the P-Glass has been removed before damage to the underlying single crystal silicon, thermal oxide, aluminum layer, etc. occurs.

Over a period of the time chart recorder produces a chart similar to that shown in FIG. 2. By examining the chart it is seen that each excursion is made up of three atomic lines, i.e., two argon lines lying at 2534.71Å and 2536.02Å in the UV spectrum. This argon doublet straddles the phosphorus atomic line 2535.65Å. This relationship is best seen in FIG. 3 which is a more resolved view of one of the excursions in FIG. 2 observed at the beginning of the etching process.

End-point, i.e., completion of the etching is completed when the atomic line for phosphorus disappears from the spectrum leaving only the argon doublet. From FIG. 2 this is seen to occur at about 3 minutes into the process for a 1 $\mu$m thick coating of P-Glass. However, the time of completion is dependent on the thickness of the P-Glass coating and other parameters within the chamber. However, in all cases the criteria for etch completion, i.e., has been found to be disappearance of the phosphorus line.

Other modification of the present invention are possible in light of the above description which should not be construed as placing any restriction on the present invention other than those limitations set forth in the claims which follow.

What is claimed is:

1. A method for detecting end-point in the plasma etching of a phosphorous doped silicon dioxide layer coated on a substrate of single crystal silicon comprising the steps of;

etching the phosphorous doped silicon dioxide from the substrate within an etching chamber with gas from the fluorinated hydrocarbon family, spectroscopically observing the gases in the etching chamber over a time interval covering the beginning and end of the etching process and within a predetermined wavelength interval, observing the presence of the phosphorous atomic line straddled by two argon atomic lines at the beginning of the etching process, observing the disappearance of said phosphorous atomic line from between said two argon atomic lines as an indication of the end of the etching process.

2. A method according to claim 1 wherein a layer of thermal oxide is disposed between the substrate and the layer of phosphorus doped silicon dioxide.

3. A method according to claim 1 wherein a layer of aluminum is disposed between the substrate and the layer of phosphorus doped silicon dioxide.

* * * * *

UNITED STATES PATENT AND TRADEMARK OFFICE
CERTIFICATE OF CORRECTION

PATENT NO. : 4,415,402
DATED : November 15, 1983
INVENTOR(S) : Barry Gelernt

It is certified that error appears in the above-identified patent and that said Letters Patent is hereby corrected as shown below:

In the title, change "END-POINT DETECTION IN PLASMA ETCHING OR PHOSPHOSILICATE GLASS" to --END-POINT DETECTION IN PLASMA ETCHING OF PHOSPHOSILICATE GLASS--.

Column 2, line 34, "turned" should be --tuned--.

Signed and Sealed this

Second Day of October 1984

[SEAL]

Attest:

Attesting Officer

GERALD J. MOSSINGHOFF

Commissioner of Patents and Trademarks